United States Patent
Wegman et al.

(10) Patent No.: US 6,387,842 B1
(45) Date of Patent: May 14, 2002

(54) PROCESS FOR PREPARING OXYGENATES AND CATALYSTS THEREFOR

(75) Inventors: Richard William Wegman, South Charleston; David Michael Minahan, Nitro; William J. Bartley; Chinsoo Stephen Lee, both of Charleston; David McNeill Somerville, Hurricane, all of WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 09/553,684

(22) Filed: Apr. 21, 2000

Related U.S. Application Data

(60) Division of application No. 09/220,438, filed on Dec. 24, 1998, now Pat. No. 6,127,432, which is a continuation-in-part of application No. 09/192,134, filed on Nov. 13, 1998, now abandoned, which is a continuation-in-part of application No. 09/015,240, filed on Jan. 29, 1998, now abandoned.

(51) Int. Cl.⁷ .............. B01J 23/00; B01J 31/00; B01J 27/14; B01J 27/19; B01J 21/12

(52) U.S. Cl. .......... 502/300; 502/308; 502/309; 502/311; 502/355; 502/155; 502/158; 502/162; 502/164; 502/170; 502/172; 502/208; 502/211; 502/218; 502/232; 502/254; 502/255; 502/257

(58) Field of Search ............ 502/300, 308–309, 502/311–355, 155, 158, 162, 164, 170, 172, 208–211, 213, 214, 218–223, 232–249, 254, 255, 257–262

(56) References Cited

U.S. PATENT DOCUMENTS 4,333,852 A * 6/1982 Warren .............. 502/162
4,357,477 A * 11/1982 Knifton .............. 568/678
4,882,360 A * 11/1989 Stevens .............. 518/714

(List continued on next page.)

FOREIGN PATENT DOCUMENTS

| EP | 0685259 | 12/1995 |
| JP | 6178933 | 8/1986 |
| JP | 62148437 | 7/1987 |
| JP | 62148438 | 7/1987 |
| JP | 01294643 | 11/1989 |

OTHER PUBLICATIONS

Arata, Kazushi, "Preparation of superacids by metal oxides for reactions of butanes and pentanes", Applied Catalysis A: General 146 (1996) 3–32 month N/A.

Momose, Hiroo et al., "Vapor–Phase Direct Hydration of Ethylene over Zirconium Tungstate Catalyst", Journal of Catalysis 77, 23–31 (1982) Jan. 1982.

Iglesia, Enrique et al., "Selective Isomerization of Alkanes on Supported Tungsten Oxide Acids", Studies in Surface Science and Catalysis, vol. 101 (1996) 533–542, Elsevier Science B.V. month N/A.

(List continued on next page.)

Primary Examiner—Mark L. Bell
Assistant Examiner—Patricia L. Hailey

(57) ABSTRACT

This invention relates in part to a processes and catalysts for the conversion of a feedstock comprising carbon monoxide and hydrogen to a product stream comprising at least one of an ester, acid, acid anhydride and mixtures thereof. This invention also relates in part to processes and catalysts for converting an alcohol, ether and/or ether alcohol feedstock to oxygenated products, e.g., esters, acids, acid anhydrides and mixtures thereof. The processes and catalysts are especially suitable for the production of acetic acid and methyl acetate from a synthesis gas feedstock or from an alcohol, ether or ether alcohol feedstock.

3 Claims, 2 Drawing Sheets

U.S. PATENT DOCUMENTS

| | | | | |
|---|---|---|---|---|
| 4,886,772 A | * | 12/1989 | Prada-Silva et al. | 502/200 |
| 5,102,845 A | * | 4/1992 | Kinkade | 502/170 |
| 5,189,203 A | | 2/1993 | Hansen et al. | 560/232 |
| 5,218,140 A | | 6/1993 | Wegman | 560/232 |
| 5,286,900 A | | 2/1994 | Hansen et al. | 560/232 |
| 5,330,955 A | | 7/1994 | Wegman | 502/210 |
| 5,420,345 A | | 5/1995 | Smith | 562/519 |
| 5,659,077 A | | 8/1997 | Macfarlan | 562/512.2 |
| 5,663,429 A | | 9/1997 | Yamaseki et al. | 562/519 |
| 5,780,383 A | | 7/1998 | Hollstein et al. | 502/324 |

OTHER PUBLICATIONS

Hino, Makoto et al., "Synthesis of Esters from Acetic Acid with Methanol, Ethanol, Propanol, Butanol, and Isobutyl Alcohol Catalyzed by Solid Superacid [1]", Chemistry Letters, pp. 1671–1672, The Chemical Society of Japan (1981) Month N/A.

Yamaguchi, Tsutomu, "Recent Progress in Solid Superacid", Applied Catalysis, 61 (1990) 1–25, Elsevier Science Publishers B.V., Amsterdam—Printed in the Netherlands Jan. 1990.

Larsen, Gustavo et al., "Tungsta and Plantinum–Tungsta Supported on Zirconia Catalysts for Alkane Isomerization", Studies in Surface Science and Catalysis, vol. 101, Elsevier Science B.V. (1996), 543–551 Month N/A.

Sardesai, Abhay et al., "Catalytic Synthesis of Methyl Acetate from Dimethyl Ether using Heteropoly Acid Catalyst", (1998) Annual Meeting Technical Program—AIChE Month N/A.

* cited by examiner

PROCESS FOR PREPARING OXYGENATES AND CATALYSTS THEREFOR

This application is a divisional of U.S. patent application Ser. No. 09/220,438, filed Dec. 24, 1998, now U.S. Pat. No. 6,127,432, which is continuation-in-part of U.S. patent application Ser. No. 09/192,134, filed Nov. 13, 1998, now abandoned, which is a continuation-in-part of U.S. patent application Ser. No. 09/015,240, filed Jan. 29, 1998, now abandoned.

BRIEF SUMMARY OF THE INVENTION

Technical Field

This invention relates in part to processes for converting carbon monoxide- and hydrogen-containing feedstocks, e.g., synthesis gas, to oxygenated products, e.g., esters, acids, acid anhydrides and mixtures thereof, and to catalysts for said processes. This invention also relates in part to processes for converting an alcohol, ether and/or ether alcohol feedstock to oxygenated products, e.g., esters, acids, acid anhydrides and mixtures thereof, and to catalysts for said processes.

BACKGROUND OF THE INVENTION

It is known that carboxylic esters, acids, anhydrides and mixtures thereof can be prepared from feedstock comprising carbon monoxide and hydrogen gases by first forming an alcohol, such as methanol, and the corresponding ether (e.g., dimethyl ether), according to the theoretical reaction:

$$2CO+4H_2=2CH_3OH \leftrightarrows (CH_3)_2O+H_2O$$

in the presence of a known alcohol conversion catalyst, and then separately converting the alcohol and/or ether in the presence of a known carbonylation catalyst into esters, acids, anhydrides and mixtures thereof containing one carbon atom more than the starting alcohol and ether, for example (theoretically):

$$CH_3OH+CO=CH_3COOH$$

or $$(CH_3)_2O+2CO+H_2O=2CH_3COOH$$

or $$CH_3OH+(CH_3)_2O+3CO+H_2O=3CH_3COOH$$

Known two step catalytic processes for producing oxygenates are described in U.S. Pat. Nos. 5,189,203 and 5,286,900. In each of the processes described in these patents, the alcohol conversion from carbon monoxide and hydrogen is carried out in a first reaction zone wherein the alcohol, and optionally the corresponding ether, are refined to a product stream and the product stream is then passed from the first reaction zone to a second reaction zone wherein the alcohol and ether are converted by a carbonylation reaction to ester, acid, anhydride or mixtures thereof As disclosed, the useful temperature and pressure ranges for carrying out the separate reactions are different. Specifically, the alcohol synthesis reactor temperatures and pressures are selected from the ranges of from about 150° C. to about 400° C. and from about 70 to 3000 psig, respectively, whereas the carbonylation reactor temperatures and pressures are selected from the ranges of from about 100° C. to about 500° C. and about 15 to 12,000 psig, respectively.

It has been disclosed that oxygenates can be produced from a synthesis gas from rhodium catalysts. JA 62/148437 and JA 62/148438 disclose the simultaneous production of acetic acid, acetaldehyde and ethanol from a synthesis gas reacted in the presence of a rhodium catalyst pretreated with sulfur-containing compounds. JA 61/178933 discloses producing oxygenates from a synthesis gas wherein the reaction is carried out in the presence of a rhodium catalyst provided with an accelerator metal such as scandium, iridium or an alkali earth metal. JA01/294643 discloses the production of oxygenated compounds such as acetic acid in which a synthesis gas is reacted in the presence of a rhodium catalyst on a silica substrate.

The cited prior art processes for producing oxygenates from a synthesis gas have taken one of two routes: a first route wherein two separate reaction zones are used—a first reaction zone to produce the alcohol, followed by separation and purification, and a second reaction zone to effectuate the carbonylation reaction to produce oxygenates, wherein the temperatures and pressures are selected from different ranges; and, a second route wherein a rhodium catalyst, contained on a substrate or treated with a specific compound (such as sulfur-containing compounds) or enhanced by an accelerator, is used to produce oxygenates and/or mixtures thereof along with aldehydes and alcohols. The first route is inefficient and capital intensive, requiring separate reaction zones, alcohol purification and complex equipment. The second route suffers from poor selectivity, resulting in a broad range of oxygenated products, because one catalytic component is being used to catalyze both reactions.

Known catalytic carbonylation processes for producing oxygenates are described in U.S. Pat. Nos. 5,218,140 and 5,330,955. Such processes involve the carbonylation of one or more alcohols, ethers and ether alcohols to esters and carboxylic acids. The processes are carried out in the vapor state over a solid catalyst comprising a polyoxometalate anion in which the metal is at least one taken from Groups 5 and 6 (such as molybdenum, tungsten, vanadium, niobium, chromium and tantalum) complexed with at least one Group 8, 9 or 10 cation (such as Fe, Ru, Os, Co, Rh, Ir, Ni, Pd and Pt).

Currently, commercial processes for the production of acetic acid from methanol and carbon monoxide employ iodide promoters which are essential to obtain an acceptable level of catalyst activity. Iodide promoters are highly corrosive, requiring the use of exotic metals in the construction of the reaction vessels and expensive processing equipment (e.g., separation and refining equipment) to recover the homogeneous promoter from the product stream.

The oxygenates industry, particularly the acetic acid industry, would benefit significantly from a process that would simplify and/or eliminate complex, expensive equipment while simultaneously enabling more control over reaction rates and product selectivity. A solution enabling these advantages would provide a highly desirable industrial advance. Improved carbonylation catalysts for making oxygenates with respect to catalyst stability and carbonylation activity and selectivity would also be a highly desirable industrial advance.

DISCLOSURE OF THE INVENTION

This invention relates in part to a process for converting a feedstock comprising carbon monoxide and hydrogen to a product stream comprising at least one of an ester, acid, acid anhydride and mixtures thereof which comprises reacting the carbon monoxide and hydrogen in the presence of a catalyst comprising an alcohol synthesis catalytic component and an alcohol carbonylation catalytic component, the composition of the components being different from one another, under conditions of temperature and pressure sufficient to produce said product stream. This process is preferably a gas or vapor phase reaction of synthesis gas to produce oxygenates therefrom, and is especially advantageous for the production of acetic acid and/or methyl acetate utilizing a single reaction vessel.

This invention also relates in part to a process for converting a feedstock comprising carbon monoxide and hydrogen to a product stream comprising at least one of an ester, acid, acid anhydride and mixtures thereof which comprises (a) reacting the carbon monoxide and hydrogen in the presence of a catalyst under conditions of temperature and pressure sufficient to produce at least one of an alcohol, ether, ether alcohol and mixtures thereof and (b) reacting carbon monoxide and said at least one of an alcohol, ether, ether alcohol and mixtures thereof in the presence of a catalyst comprising a solid super acid, clay, zeolite or molecular sieve under conditions of temperature and pressure sufficient to produce said product stream. This process is preferably a gas or vapor phase reaction, and is especially advantageous for the production of acetic acid and/or methyl acetate utilizing separate reaction vessels for steps (a) and (b).

This invention further relates in part to a process for converting a feedstock comprising at least one of an alcohol, ether, ether alcohol and mixtures thereof to a product stream comprising at least one of an ester, acid, acid anhydride and mixtures thereof by reacting carbon monoxide and said at least one of an alcohol, ether, ether alcohol and mixtures thereof in the presence of a catalyst comprising a solid super acid, clay, zeolite or molecular sieve under conditions of temperature and pressure sufficient to produce said product stream. This process is preferably a gas or vapor phase reaction, and is especially advantageous for the production of acetic acid and/or methyl acetate utilizing one or more reaction vessels.

This invention yet further relates in part to a multicomponent catalyst comprising (a) a first component capable of catalyzing a reaction of carbon monoxide and hydrogen to produce at least one of an alcohol, ether, ether alcohol and mixtures thereof and, (b) a second component having a composition different from that of the first component and capable of catalyzing a reaction of carbon monoxide and said at least one alcohol, ether, ether alcohol and mixtures thereof produced in the presence of the first component to produce at least one of an ester, acid, acid anhydride and mixtures thereof This invention also relates in part to a solid catalyst for the carbonylation of a feedstock comprising at least one of an alcohol, ether, ether alcohol and mixtures thereof to a product stream comprising at least one of an ester, acid, acid anhydride and mixtures thereof, by reaction thereof in the vapor state, said catalyst selected from a solid super acid, clay, zeolite or molecular sieve.

The processes and catalysts of this invention are particularly unique in that they enable the production of oxygenates from carbon monoxide- and hydrogen-containing feedstocks or alcohol, ether or ether alcohol feedstocks in one or more reactors and in which no halides are required in the liquid or vapor phases of the feedstock streams and/or recycle streams of the processes, thus providing substantial economic benefits in the design of equipment to carry out the processes. Moreover, the multicomponent catalysts of this invention enable substantial control over the composition of the reaction product simply by varying the composition of one component of the catalyst and/or its concentration relative to the other component. Further, the processes and catalysts of this invention enable the production of oxygenates under one or more sets of reaction conditions. The carbonylation catalysts of this invention provide improved catalyst stability and improved carbonylation activity and selectivity as described herein. In a preferred embodiment, the alcohol producing reaction, i.e., step (a) above, and carbonylation reaction, i.e., step (b) above, can be carried out in separate reactors and each reactor can be operated at different reaction conditions. The product stream exiting the alcohol synthesis reactor can be fed directly into the carbonylation reactor.

DETAILED DESCRIPTION

Figure 1:
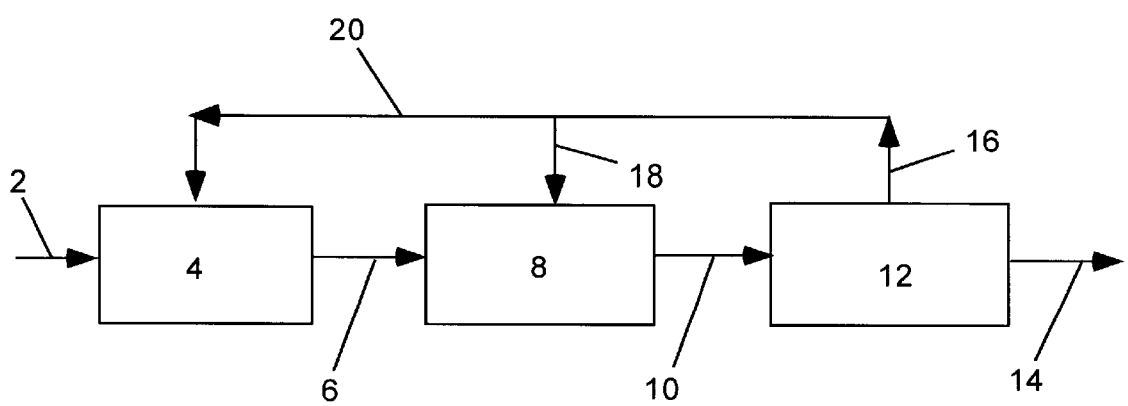
FIG. 1 is a schematic representation of a one-reactor process flow diagram to make acetic acid from a feedstock gaseous mixture comprising carbon monoxide and hydrogen gases prepared from a hydrocarbon feed to a "synthesis gas" or "syn gas" generator.

According to one embodiment of this invention, a feedstock comprising carbon monoxide and hydrogen is converted to a product stream comprising at least one of an ester, acid, acid anhydride and mixtures thereof by reacting the carbon monoxide and hydrogen, in the presence of a catalyst, to convert the same to the product stream, wherein the catalyst comprises an alcohol synthesis catalytic component and an alcohol carbonylation catalytic component. In particular, a gaseous feedstock comprising carbon monoxide and hydrogen gases is converted to the product stream in a vapor phase, controlled temperature and pressure, reaction in the presence of a solid catalyst comprising a metal based alcohol synthesis catalytic component and an alcohol carbonylation catalytic component.

More particularly, the gas feedstock is converted to the product stream in the presence of a solid catalyst comprising a metal based alcohol synthesis catalytic component and a heterogeneous alcohol carbonylation catalytic component. Preferably, such processes yield a product stream comprising at least one of acetic acid, methyl ester, acetic anhydride and mixtures thereof and is carried out in the presence of a solid catalyst system comprising a metal-based alcohol synthesis catalytic component and a solid super acid alcohol carbonylation catalytic component. More preferably, a synthesis gas feedstock is converted substantially to acetic acid in a vapor phase, catalyzed, temperature and pressure controlled reaction wherein the catalyst is a solid catalyst consisting essentially of a metal-based alcohol synthesis catalytic component and a solid super acid impregnated with a Group 7, 8, 9, 10 and/or 11 metal.

This embodiment is simple and unique. The processes to produce the product stream are carried out in a single reaction zone in the presence of a multicomponent catalyst whose composition can be varied by changing the catalytic components so as to control the rate and selectivity of the first and/or second reactions, thereby effectively controlling the composition of the product stream and the rate of production of the stream constituents. In a preferred embodiment of such processes, the multicomponent catalyst is a solid catalyst consisting essentially of a metal-based alcohol synthesis catalytic component and a heterogeneous alcohol carbonylation component. The unique catalyst enables highly selective and rate controllable processes which can be carried out under a singular set of reaction condition temperatures and pressures. The multicomponent catalyst may comprise one or more catalyst beds in a single reaction vessel, e.g., a dual bed catalyst which comprises one bed containing the alcohol synthesis catalytic component and another separate bed containing the alcohol carbonylation catalytic component, or a single bed catalyst mixture, e.g., a mixture of the alcohol synthesis catalytic component and the alcohol carbonylation catalytic component.

It has been discovered that hydrogen or a feedstock containing hydrogen, e.g., synthesis gas, has an unexpected stabilizing effect on the heterogeneous alcohol carbonylation catalytic component of the catalyst as compared to reactions in which only methanol and carbon monoxide are present in the system as described more fully below. This unexpected effect is especially valuable for the production of acetic acid.

In another embodiment, this invention is directed to processes and catalysts for converting a feedstock comprising carbon monoxide and hydrogen to a product stream comprising at least one of an ester, acid, anhydride and mixtures thereof, which comprises (a) reacting the carbon monoxide and hydrogen in the presence of a catalyst under conditions of temperature and pressure sufficient to produce at least one of an alcohol, ether, ether alcohol and mixtures thereof and (b) reacting carbon monoxide and said at least one of an alcohol, ether, ether alcohol and mixtures thereof in the presence of a catalyst comprising a solid super acid, clay, zeolite or molecular sieve and under conditions of temperature and pressure sufficient to produce said product stream. In this embodiment, the processes are preferably carried out in two linked reaction vessels with the first reaction vessel containing the alcohol synthesis catalyst and the second reaction vessel containing the carbonylation catalyst.

As with the multicomponent catalyst above, it has been discovered that hydrogen or a feedstock containing hydrogen, e.g., synthesis gas, has an unexpected stabilizing effect on the carbonylation catalyst employed in step (1) above as compared to reactions in which only methanol and carbon monoxide are present in the system as described more fully below. This unexpected effect is especially valuable for the production of acetic acid.

An illustrative overall reaction of the processes of this invention in a single reaction zone can be represented as follows:

wherein R is an alkyl group from 1 to about 12 carbon atoms, and R' is hydrogen or an alkyl group from 1 to about 12 carbon atoms, and wherein m is an integer of 1 or 2, n is 0 when m is 2, and n is 1 when m is 1, x and y are the stoichiometric coefficients for a particular reaction, and z is one less than the number of carbon atoms of R.

Another illustrative overall reaction of the processes of this invention in separate reaction zones can be represented as follows:

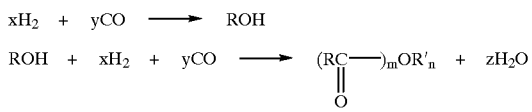

wherein R is an alkyl group from 1 to about 12 carbon atoms, and R' is hydrogen or an alkyl group from 1 to about 12 carbon atoms, and wherein m is an integer of 1 or 2, n is 0 when m is 2, and n is 1 when m is 1, x and y are the stoichiometric coefficients for a particular reaction, and z is one less than the number of carbon atoms of R.

Processes for reforming hydrocarbons to produce synthesis gas are well known. Each has its advantages and disadvantages and the choice of using a particular reforming process is dictated by economic and available feed stream considerations, as well as by the desired mole ratio of $H_2$:CO in the feedstock resulting from the reforming reaction. Steam reforming typically produces a hydrogen to carbon monoxide mole ratio greater than about 2.5:1. Partial oxidation reforming can typically produce smaller hydrogen to carbon monoxide mole ratios. Partial oxidation reforming of alkane is a controlled combustion reaction in which a feed stream of alkane hydrocarbon, such as methane, and oxygen is introduced into a combustion chamber. The combustion conditions are controlled to selectively make the desired hydrogen-carbon monoxide ratio in the feedstock. Steam reforming and partial oxidation of hydrocarbons are well known processes and are described, for example, in Kirk-Othmer, Encyclopedia of Chemical Technology, Fourth Edition, 1996, the pertinent portions of which are incorporated herein by reference.

Any hydrocarbon-containing feed stream that can be converted into a feedstock comprising carbon monoxide and hydrogen, most preferably a synthesis gas (or "syn gas"), is useful in the processes of the invention. The ratio of hydrogen to carbon monoxide in the reaction zone is in the range of about 50:1 to 1:50, preferably in the range of about 20:1 to 1:20, more preferably in the range of about 10:1 to 1:10. Useful feed streams include natural gas (mainly methane, but natural gas composition can vary depending on location and source), naphtha, refinery off-gas, LPG, gas oil, vacuum residuals, shale oils, asphalts, various types of fuel oils, and hydrocarbon containing process recycle streams. In a preferred embodiment, methanol can be converted into feed components comprising carbon monoxide and hydrogen, e.g., synthesis gas. Further, hydrogen may be formed in situ, for example, by water-gas shift.

Feedstocks comprising carbon monoxide and hydrogen, e.g., synthesis gas, may undergo purification prior to being fed to any reaction zones. For use in the processes of this invention, the synthesis gas should be essentially free of catalyst poisons and inhibitors such as hydrogen sulfide, carbonyl sulfide, metal carbonyls, e.g., iron carbonyl and nickel carbonyl, ammonia, basic organic compounds, e.g., methyl amine and ethyl amine, and generally any compounds that will neutralize an acid. Synthesis gas purification may be carried out by processes known in the art. See, for example, Weissermel, K. and Arpe H.-J., Industrial Organic Chemistry, Second, Revised and Extended Edition, 1993, pp. 19–21.

The particular reaction conditions for both the single reactor and separate reactor embodiments described below are not narrowly critical and can be any effective reaction conditions sufficient to produce at least one of an ester, acid, acid anhydride and mixtures thereof. The exact reaction conditions will be governed by the best compromise between achieving high catalyst selectivity, activity, lifetime and ease of operability, as well as the intrinsic reactivity of the starting materials in question and the stability of the starting materials and the desired reaction product to the reaction conditions.

In one embodiment of this invention, feedstock comprising the desired molar ratio of $H_2$:CO is fed to a single reactor at a controlled rate and the reaction is carried out in a reaction zone under controlled conditions of temperature and pressure in the presence of a catalyst to convert the feedstock into one or more oxygenates. The temperature in the reaction zone is selected from the range of from about 100° C. to about 500° C., preferably a temperature in the range of from about 150° C. to about 400° C., with an especially preferred temperature in the range of from about 175° C. to about 375° C. The gas hourly space velocity (GHSV) of the feedstock (liters of feedstock/hr/liter of catalyst) passing through the reaction zone can vary significantly, depending upon a variety of factors such as, for example, reaction conditions, composition of the feedstock and quantity and type of catalyst being used. The GHSV can be maintained at any rate in the range of from about 1 to about 30,000 $hr^{-1}$ or more, preferably will be maintained at a rate of at least about 500 $hr^{-1}$, and more preferably will be maintained at a rate of at least 1,000 $hr^{-1}$.

The pressure in the single reaction zone may be selected from the range of from about 1 to about 10,000 psig, preferably a pressure in the range of from about 50 to about 5,000 psig, with an especially preferred pressure in the range of from about 500 to about 3,000 psig. The hydrogen and carbon monoxide partial pressures should be sufficient to enable the production of one or more oxygenates. Additionally, the hydrogen partial pressure should be sufficient to impart stabilization to the carbonylation catalytic component. Illustrative hydrogen partial pressures may range, for example, from about 0.1 psig or less to about 9000 psig or greater, or from about 0.1 psig or less to about 4500 psig or greater, or from about 0.1 psig or less to about 2700 psig or greater. Illustrative carbon monoxide partial pressures may range, for example, from about 0.1 psig or less to about 9000 psig or greater, or from about 0.1 psig or less to about 4500 psig or greater, or from about 0.1 psig or less to about 2700 psig or greater. Hydrogen and carbon monoxide may be fed separately to the single reactor or in combination, e.g., synthesis gas.

In another embodiment of this invention, when the alcohol producing reaction and carbonylation reaction are carried out in separate reaction vessels, a feedstock comprising the desired molar ratio of $H_2$:CO is fed to the alcohol producing reactor at a controlled rate and the reaction is carried out in a reaction zone under controlled conditions of temperature and pressure in the presence of a catalyst to convert the feedstock into one or more alcohols, ethers, ether alcohols and mixtures thereof. Such reactions may be carried out by conventional methods known in the art. See, for example, U.S. Pat. Nos. 5,189,203 and 5,286,900. The product stream exiting the alcohol reactor may then be fed to the carbonylation reactor at a controlled rate and the reaction is carried out in a reaction zone under controlled conditions of temperature and pressure in the presence of a catalyst as defined herein to convert the feedstock into one or more oxygenates.

The temperature in the carbonylation reaction zone is selected from the range of from about 100° C. to about 500° C., preferably a temperature in the range of from about 150° C. to about 400° C., with an especially preferred temperature in the range of from about 175° C. to about 375° C. The gas hourly space velocity (GHSV) of the feedstock (liters of feedstock/hr/liter of catalyst) passing through the carbonylation reaction zone can vary significantly, depending upon a variety of factors such as, for example, reaction conditions, composition of the feedstock and quantity and type of catalyst being used. The GHSV can be maintained at any rate in the range of from about 1 to about 30,000 $hr^{-1}$ or more, preferably will be maintained at a rate of at least about 500 $hr^{-1}$, and more preferably will be maintained at a rate of at least 1,000 $hr^{-1}$. Likewise, the liquid hourly space velocity (LHSV) of the feedstock passing through the carbonylation reaction zone can vary significantly, depending upon a variety of factors such as, for example, reaction conditions, composition of the feedstock and quantity and type of catalyst being used. The LHSV to the reactor when the feed is vaporized prior to entering or within the reactor may range from about 0.001 to about 100 $hr^{-1}$, preferably from about 0.01 to about 10 $hr^{-1}$. The GHSV and LHSV accommodate the amount of alcohol, ether, ether alcohol and mixtures thereof fed to the carbonylation reactor.

The pressure in the carbonylation reaction zone may be selected from the range of from about 1 to about 10,000 psig, preferably a pressure in the range of from about 50 to about 5,000 psig, with an especially preferred pressure in the range of from about 500 to about 3,000 psig. The carbon monoxide partial pressure should be sufficient-to permit the reaction with an alcohol, ether, ether alcohol or mixtures thereof to produce one or more oxygenates. The hydrogen partial pressure should be sufficient to impart stabilization to the carbonylation catalyst. Illustrative hydrogen partial pressures may range, for example, from about 0.1 psig or less to about 9000 psig or greater, or from about 0.1 psig or less to about 4500 psig or greater, or from about 0.1 psig or less to about 2700 psig or greater. Illustrative carbon monoxide partial pressures may range, for example, from about 0.1 psig or less to about 9000 psig or greater, or from about 0.1 psig or less to about 4500 psig or greater, or from about 0.1 psig or less to about 2700 psig or greater. Hydrogen and/or carbon monoxide may be fed separately to the carbonylation reactor or in combination, e.g., as synthesis gas or as part of a feed stream from a separate reactor as described herein. In a preferred embodiment, methanol can be converted into feed components comprising carbon monoxide and hydrogen, e.g., synthesis gas.

For purposes of this invention, GHSV is gas hourly space velocity which is the rate of gas flow over the catalyst. It is determined by dividing the volume of gas (at 25° C. and 1 atmosphere) which passes over the catalyst in one hour by the volume of the catalyst. LHSV is liquid hourly space velocity which is the rate that the liquid organic substrate is fed to the carbonylation reactor. It is determined by dividing the liquid volume pumped in one hour by the volume of catalyst.

The carbonylation reaction can be carried out by passing the substrate to be carbonylated and carbon monoxide and optionally hydrogen over the catalyst as a vapor phase reaction or as a liquid phase reaction, e.g., slurry reaction. The substrate comprising an alcohol, ether, ether alcohol or mixtures thereof can be formed in situ by feeding synthesis gas to an appropriate catalyst that is coupled to the carbonylation catalyst either in the same or different reactors. If desired, such substrates, e.g., methanol, and/or synthesis gas can be obtained from a different source and fed directly to the carbonylation catalyst.

The alcohol synthesis catalyst or alcohol synthesis catalytic component is selected from either of two groups: a first group which includes: (a) alkali and/or metal promoted MoS$_2$-based materials, (b) Group 7, 8, 9, 10 and/or 11 metals, supported or unsupported, with or without metal and alkali promoters, (c) mixed metal oxides of Co or Ni with Cu with or without a trivalent metal ion and/or alkali promoters, and (d) mixtures thereof; and a second group which includes (a) an alkali and/or metal promoted ZnCrO, MnCro and ZnMnCrO, (b) alkali and/or metal promoted Cu/ZnO materials, and (c) mixtures thereof, and mixtures of the first and second groups. Preferably, the alcohol synthesis catalyst or alcohol synthesis catalytic component is selected from among those catalysts used commercially to make methanol from a synthesis gas, which are highly developed and their activity and selectivity are known. They include: (a) Cu/ZnO (with or without Al), (b) Cu-rare earth metals, and (c) supported Group 7, 8, 9 and/or 10 metals. These catalysts generate methanol from a synthesis gas according to the following reaction:

$$2H_2 + CO \rightleftharpoons CH_3OH$$

Alcohol synthesis catalysts or alcohol synthesis catalytic components that typically generate from synthesis gas an Anderson-Schultz-Flory product distribution of linear alcohols include (a) alkali and/or metals promoted MoS$_2$-based materials, (b) Group 7, 8, 9 and/or 10 metals, with or without metal promoters and alkali, and (c) mixed metal oxides of Co or Ni and Cu, with or without a trivalent metal ion and/or alkali promoters. These catalysts or catalytic components generate linear alcohols from synthesis gas according to the following reaction:

$$xH_2 + yCO \rightleftharpoons R\text{---}CH_2OH + zH_2O$$

where x, y and z are the required stoichiometric coefficients, and R is H or an alkyl group of 1 to about 12 carbon atoms. Linking together the alcohol synthesis catalyst and alcohol carbonylation catalyst from separate reactors or coupling the alcohol synthesis catalytic component with the alcohol carbonylation catalytic component in a single reactor yields linear carboxylic acids according to the overall reaction:

$$xH_2 + yCO \rightarrow RCH_2C(O)OH + zH_2O$$

where x, y and z are the required stoichiometric coefficients, and in R is H or an alkyl group of 1 to about 12 carbon atoms.

Alcohol catalysts and alcohol catalytic components that typically generate from synthesis gas a non-Anderson-Schultz-Flory distribution of methanol, ethanol and 2-methyl branched higher alcohols, e.g., isobutanol, include (a) alkali and/or metal promoted ZnCrO, MnCrO and ZnMnCrO, and (b) alkali and/or metal promoted Cu/ZnO materials. These catalysts and catalytic components generate branched alcohols according to the following reaction:

$$xH_2 + yCO \rightleftharpoons R\text{---}\underset{CH_3}{CHCH_2OH} + zH_2O$$

where x, y and z are the required stoichiometric coefficients, and R is H or an alkyl group of 1 to about 12 carbon atoms. Linking together the alcohol synthesis catalyst and alcohol carbonylation catalyst from separate reactors or coupling the alcohol synthesis catalytic component with the alcohol carbonylation catalytic component in a single reactor yields non-linear carboxylic acids according to the overall reaction:

$$xH_2 + yCO \rightarrow R\text{---}\underset{CH_3}{CHCH_2COOH} + zH_2O$$

where x, y and z are the required stoichiometric coefficients, and R is H or an alkyl group of 1 to about 12 carbon atoms.

In the embodiment of this invention which involves converting a feedstock comprising at least one alcohol, ether, ether alcohol or mixtures thereof to a product stream comprising at least one of an ester, acid, acid anhydride and mixtures thereof, suitable feedstocks may include, for example, mono- and polyhydric alcohols, alkylethers such as alkyl or alkylene mono- and polyethers, and alkyl ether alcohols and mixtures thereof. Such compounds may contain aromatic rings. The preferred alcohols, ethers and ether alcohols that may be carbonylated by the processes of this invention include alkanols of 1 to about 20 carbon atoms, alkane polyols of 2 to about 24 carbon atoms, alkyl monoethers of 2 to about 20 carbon atoms, alkyl alkylene polyethers of 4 to about 40 carbon atoms and alkoxyalkanols of 3 to about 20 carbon atoms. Illustrative alcohols, ethers and ether alcohols that may be carbonylated in accordance with this invention are disclosed in U.S. Pat. Nos. 5,218,140 and 5,330,955, the disclosures of which are incorporated herein by reference. The feedstocks comprising at least one alcohol, ether, ether alcohol or mixtures thereof may be prepared as described herein or alternatively may be obtained from a different source and fed directly to the carbonylation catalyst.

In such carbonylation embodiment, the processes involve providing at least one of the alcohol, ether, ether alcohol and mixtures thereof in the vapor state and passing the vapor over a bed containing the solid catalyst comprising a super acid, clay, zeolite, or molecular sieve under conditions described above. Preferably, the solid super acid, clay, zeolite and molecular sieve are impregnated with a Group 7, 8, 9, 10 and/or 11 metal as described herein.

The carbonylation reaction may be carried out in a tubular reactor using a fixed bed of the catalyst. The reactants may be fed to the catalyst by feeding down or up, or a combination of both, to a fixed bed located in a tubular reactor. It may be desirable to use a reactor design that operates by plug flow and causes minimal turbulence in the reactor zone. The carbonylation reaction may be effected in a dynamic bed of the catalyst. In such a reaction, the bed of catalyst is moving such as in the case of a fluid bed of the catalyst.

Where the alcohol, ether, ether alcohol reactant is a higher boiling material not easily vaporized, it can be diluted with a lower boiling nonreactive solvent or diluent and thus transported over the solid catalyst. The degree of dilution in some cases can be quite extreme and of course, such conditions will adversely affect the cost of carbonylation. Suitable solvents and diluents include aliphatic and aromatic hydrocarbons, esters, non-condensable ketones, and the like.

The alcohol carbonylation catalysts and alcohol carbonylation catalytic components useful in the processes of this invention include solid acidic materials, for example, solid super acids, heteropoly acids, clays, zeolites, molecular sieves, and the like. Two or more permissible alcohol carbonylation catalysts or alcohol carbonylation catalytic components may be used in a combined form. Illustrative of suitable alcohol carbonylation catalysts and alcohol carbonylation catalytic components include those permissible solid acidic materials described in Tsutomu Yamaguchi, "Recent Progress in Solid Superacid", Applied Catalysis, 61, (1990), 1 and "Zeolite, Clay, and Heteropoly Acid in Organic Reactions", by Yusuke Izumi, Kazuo Urabe and Makato Onaka, VCH Publishers Inc., 1992, the pertinent portions of which are incorporated herein by reference.

The alcohol carbonylation catalysts and alcohol carbonylation catalytic components exhibit an acid strength of less than or equal to −5.0 (Ho≦−5.0), preferably less than or equal to −10.0 (Ho≦−10.0), and more preferably less than or equal to −12.5 (Ho≦−12.5). Acid strength of solid acids can be evaluated by conventional methods such as by establishing Hammett acidity functions (Ho) using organic indicators as described below.

When the color of a catalyst sample subjected to the determination is white, this sample is immersed in benzene and a benzene solution containing an acid-base indicator of a known pKa value is added thereto. The sample is kept under observation until the indicator on the surface of the sample assumes the color of acidity. The smallest value of pKa at which the color of acidity is assumed is reported as the acid strength of the sample. The indicators (pKa) which are usable for this determination include, for example, m-nitrotoluene (−12.0), p-nitrotoluene (−12.4), p-nitrochlorobenzene (−12.7), m-nitrochlorobenzene (−13.2), 2,4-dinitrotoluene (−13.8), and 1,3,5-trinitrobenzene (−16.0).

Solid super acid catalysts are preferred carbonylation catalysts and carbonylation catalytic components for use in this invention. The preferred solid super acids have an acidity stronger than 100% $H_2SO_4$, i.e., Ho<−12.5. Illustrative examples of solid super acids are $Fe_2O_3$—$SO_4$, $SnO_2$—$SO_4$, $TiO_2$—$SO_4$, $ZrO_2$—$SO_4$ and $ZrO_2$—$B_2O_3$, $ZrO_2$—$MO_3$, $ZrO_2$—$WO_3$, $Fe_2O_3$—$WO_3$, sulfated metal oxides promoted with Pt, Fe, Mn, and halogen promoted $SiO_2$/alumina. A solid super acid impregnated with a Group 7, 8, 9, 10 and/or 11 transition metal is a particularly preferred catalyst or catalytic component. Illustrative of suitable solid super acids include those permissible solid super acids described in Tsutomu Yamaguchi, "Recent Progress in Solid Superacid", Applied Catalysis, 61, (1990), 1, supra.

The solid super acids and methods for their preparation are known. See, for example, EP Patent Application 0 685 259 A2 and U.S. Pat. No. 5,780,383, the disclosures of which are incorporated herein by reference. Preferred alcohol carbonylation catalysts and catalytic components are obtained when certain solid super acids such as Group 4, 5 and/or 6 metal oxides and mixtures thereof are impregnated with a Group 7, 8, 9, 10 and/or 11 metal and mixtures thereof. The weight percent of Group 7, 8, 9, 10 and/or 11 metals impregnated onto Group 4, 5 and/or 6 metal oxides can range from about zero to about 10 weight percent or greater, preferably from about 0.001 weight percent to about 5 weight percent. The weight percent of Group 6 metal oxides, i.e., $MoO_3$ and $WO_3$, in said Group 4, 5 and/or 6 metal oxide super acids can range from about 1 to about 40 weight percent or greater, preferably from about 10 weight percent to about 30 weight percent. The catalysts carbonylate methanol, dimethyl ether, and methyl acetate with synthesis gas in the vapor phase or in the liquid phase, e.g., as a slurry.

As indicated above, no halides, e.g., methyl iodide, are required in the liquid or vapor phases of the feedstock streams and/or recycle streams of the processes of this invention, thus providing substantial economic benefits in the design of equipment to carry out the processes. It is understood that halides which are fixed onto the catalyst or otherwise are an integral part of the catalyst are permissible in the processes of this invention.

The preferred solid super acids are based on Group 4 metal oxides impregnated with Mo or W. Thus, the preferred solid super acids are mixtures of Ti—W, Ti—Mo, Zr—W, Zr—Mo, Hf—W, and Hf—Mo oxides. Mixtures of the oxides, such as Zr—W—Ti or Ti—Mo—Hf, are also useful solid super acid catalysts Tungsten oxide, molybdenum oxide, or tungsten-molybdenum composite oxide/zirconium oxide super acids are also preferred. These solid super acids are expressed as $WO_3$/$ZrO_2$, $MoO_3$/$ZrO_2$, and $WO_3$—$MoO_3$/$ZrO_2$. Solid super acids of tungsten oxide/tin oxide, titanium oxide, iron oxide, or composite oxide of at least two elements selected among tin, titanium and iron are further preferred. These solid super acids are expressed as $WO_3$/$SnO_2$, $WO_3$/$TiO_2$, $WO_3$/$Fe_2O_3$, $WO_3$/$SnO_2$—$TiO_2$, $WO_3$/$SnO_2$—$Fe_2O_3$, $WO_3$/$TiO_2$—$Fe_2O_3$, and $WO_3$/$SnO_2$—$TiO_2$—$Fe_2O_3$ The solid super acids can serve as the support in addition to serving as an integral part of the catalyst. A preferred catalyst and catalytic component consists of a manufactured solid super acid pellet that is impregnated by an appropriate Group 7, 8, 9, 10 and/or 11 metal.

Supported catalysts are also useful in this invention. For example, an active catalyst may be obtained by loading Group 4 or 5, Mo or W precursors onto alumina, silica, various clays, etc., and then transforming (via calcination) the precursors into a supported solid acid. This material may then be impregnated with the Group 7, 8, 9, 10 and/or 11 metal. The Group 9 and 10 metals yield particularly active catalysts. The preferred Group 9 and 10 metals are Ir, Pd and Pt. The solid super acids impregnated with a Group 7, 8, 9, 10 and/or 11 metal can be used separately or as a mixture and exhibit good selectivity and thermal stability. Pd—$ZrO_2$—$WO_3$ is a preferred solid super acid catalyst for use in this invention.

As indicated above, it has been discovered that hydrogen or a feedstock containing hydrogen, e.g., synthesis gas, has an unexpected stabilizing effect on the heterogeneous alcohol carbonylation catalyst and alcohol carbonylation catalytic component as compared to reactions in which only methanol and carbon monoxide are present in the system. While not wishing to be bound to any particular mechanism or theory, it is believed that the presence of hydrogen may play an important role in generating an active alcohol carbonylation catalyst and alcohol carbonylation catalytic component by means of hydrogen spillover, i.e., hydrogen atoms migrate (spill over) from the metal to the metal oxide surface forming acidic sites where carbonylation occurs. This stabilizing effect is particularly beneficial for alcohol carbonylation catalysts and alcohol carbonylation catalytic components such as $ZrO_2$—$WO_3$ impregnated with low levels Group 7, 8, 9, 10 and/or 11 metals, e.g., Pd, Pt, Rh, Ir, Ru, Re and Os. Illustrative metals which promote this stabilizing effect include Group 7, 8, 9, 10 and 11 metals, e.g., Ag, Cu, physical mixtures of Pd, Pt, Rh, Ir, Ru, Os supported on $Al_2O_3$ or $SiO_2$ physically mixed with a Group 4 solid super acid and the like.

The amount of hydrogen is not narrowly critical and should preferably be an amount sufficient to impart the desired stabilizing effect on the heterogeneous alcohol carbonylation catalyst and alcohol carbonylation catalytic component. Suitable hydrogen partial pressures may range, for example, from about 0.1 psig or less to about 9000 psig or greater, or from about 0.1 psig or less to about 4500 psig or greater, or from about 0.1 psig or less to about 2700 psig or greater. Hydrogen may be fed separately to the carbonylation reactor or in combination with other feedstock components, e.g., as synthesis gas or as part of a feed stream from a separate reactor as described herein.

Other illustrative solid super acids useful in this invention include sulfuric acid-carried solid super acids such as disclosed in EP Patent Application 0 685 259 A2. As typical examples of these kinds, the following solid super acids may be cited:

(1) solid super acids of $SO_4$/oxide of a metal of Groups 4 and 14, e.g., $SO_4$/zirconium oxide, $SO_4$/titanium oxide, $SO_4$/tin oxide and $SO_4$/hafnium oxide, represented as $SO_4/ZrO_2$, $SO_4/TiO_2$, $SO_4/SnO_2$ and $SO_4/HfO_2$ respectively.

(2) $SO_4$/iron oxide solid super acid, e.g., $SO_4/Fe_2O_3$.

(3) $SO_4$/silicon oxide solid super acid, e.g., $SO_4/SiO_2$.

(4) $SO_4$/aluminum oxide solid super acid, e.g., $SO_4/Al_2O_3$.

Another category of alcohol carbonylation catalysts and catalytic components include heteropoly acids such as disclosed in U.S. Pat. Nos. 5,218,140 and 5,330,955, supra. Preferred heteropoly acids exhibit an acid strength of less than or equal to −1.0 (Ho≦−1.0), preferably less than or equal to −5.0 (Ho≦−5.0). Such alcohol carbonylation catalysts and catalytic components contain a polyoxometalate ion in which a metal, or mixture of metals, selected from Groups 4, 5, 6 and 7 metals is complexed with a cation from a member of Group 7, 8, 9, 10 and/or 11 metals. More preferably this alcohol carbonylation catalyst and catalytic component consists of a Group 7, 8, 9, 10 and/or 11 metal cation complexed with a heteropoly acid anion. Mixtures of heteropoly acids may be employed in the processes of this invention. The preferred heteropoly acids are represented by the formulae:

$$M_a Q_b O_c$$

or $$M_a Q_b O_c Z_d$$

or mixtures thereof wherein M is at least one metal selected from Group 7, 8, 9, 10 and/or 11 metals, Q is one or more of a Group 4, 5 and/or 6 metal, e.g., tungsten, molybdenum, vanadium, niobium, chromium and tantalum, O is oxygen, Z is one or more of phosphorus, arsenic, silicon or antimony, and   and $d$ are each integers having values sufficient to fulfill the molecular stoichiometry. In particular, $a$ is an integer having a value of from 1 to about 5 or greater $b$ is an integer having a value of from 1 to about 20 or greater, $c$ is an integer having a value of from 1 to about 60 or greater, and $d$ is a value having a value of from 1 to about 5 or greater.

More particularly, one such heterogeneous alcohol carbonylation catalyst and catalytic component is $M[Q_{12}ZO_{40}]$, wherein M is a Group 7, 8, 9, 10 and/or 11 metal, or a combination of Group 7, 8, 9, 10 and/or 11 metals, Q is one or more of Group 4, 5 and/or 6 metals, e.g., tungsten, molybdenum, vanadium, niobium, chromium, and tantalum, Z is phosphorus, antimony, silicon or arsenic, and 0 is oxygen. A more preferred embodiment of this alcohol carbonylation catalyst and catalytic component is $M[Q_{12}PO_{40}]$, where M is Rh, Pd, Co, Ir, Ru and combinations thereof, and Q is tungsten or molybdenum. A most preferred embodiment of this alcohol carbonylation catalyst and catalytic component is $MW_{12}PO_{40}$, wherein M is Ir, Ru, Rh, Pd and combinations thereof. Other preferred heteropoly acids include phosphorous tungstate and/or an alkali metal salt thereof. These heteropoly acids are expressed as $H_3P_1W_{12}O_{40}$ and $H_{3-x}A_xP_1W_{12}O_{40}$, wherein A is an alkali metal (sodium, potassium, rubidium, and/or cesium) and x is above 0 and below 3 (0<x<3). Illustrative of suitable heteropoly acids include those permissible heteropoly acids described in "Zeolite, Clay, and Heteropoly Acid in Organic Reactions", by Yusuke Izumi, Kazuo Urabe and Makato Onaka, VCH Publishers Inc., 1992, supra.

Other useful alcohol carbonylation catalysts include clays. Clays may also serve as a support for the alcohol carbonylation catalysts. Preferred clays exhibit an acid strength of less than or equal to −1.0 (Ho≦−1.0), preferably less than or equal to −5.0 (Ho≦−5.0). The weight percent of Group 7, 8, 9, 10 and/or 11 metals that may be impregnated onto clays can range from about zero to about 10 weight percent, preferably from about 0.001 weight percent to about 5 weight percent. Clay is a label applied to a generic class of materials comprised of layers of aluminosilicate with complex intercalation chemistry. In general, the layers have an overall negative charge which is balanced by hydrated cations occupying the interlayer space. The acidity of clays can be modified by exchanging the interlayer cations. The strong acidity of clays originates in the dissociation of surface Si—OH groups and from the intercalated cations. Ion exchange with suitable large inorganic cations leads to pillared clays, which can be potential shape selective catalysts. Preferred pillared clays have increased surface areas and thermal stability. Careful selection of cations for clay ion exchange can lead to pillared clays with large well defined spaces between layers (referred to as galleries), that can be useful as selective catalysts. Suitable clays useful in this invention include, for example, montmorillonite, bentonite, kaolinite, and the like, including mixtures thereof. Illustrative of suitable clays include those permissible clays described in "Zeolite, Clay, and Heteropoly Acid in Organic Reactions", by Yusuke Izumi, Kazuo Urabe and Makato Onaka, VCH Publishers Inc., 1992, supra.

Still other useful alcohol carbonylation catalysts include molecular sieves of the zeolitic variety, i.e., zeolites, and molecular sieves of the non-zeolitic variety, i.e., molecular sieves. Preferred zeolites and molecular sieves exhibit an acid strength of less than or equal to −1.0 (Ho≦−1.0), preferably less than or equal to −5.0 (Ho≦−5.0). The weight percent of Group 7, 8, 9, 10 and/or 11 metals that may be impregnated onto zeolites and molecular sieves can range from about zero to about 10 weight percent, preferably from about 0.001 weight percent to about 5 weight percent. Illustrative zeolites useful in this invention include, for example, LZ-10, LZ-20, 4A, 5A, 13X, 10X, Y, SK40, SK41, chabazite, faujasite, levynite, gismondine, erionite, sodalite, analcime, gmelinite, harmotome, mordenite, epistilbite, heulandite, stilbite, edingtonite, mesolite, natrolite, scolecite, thomsonite, brewsterite, laumontite, phillipsite, the ZSM's (ZSM-5, ZSM-20, ZSM-12, and ZSM-34), and the like, including mixtures thereof. Illustrative zeolites useful in this invention are disclosed in U.S. Pat. Nos. 3,702,886, 3,972,983, 3,832,449, 4,086,186 and 3,308,069, the disclosures of which are incorporated herein be reference.

Illustrative molecular sieves useful in this invention include, for example, the silica molecular sieves, such as silicalite (S115) as depicted in U.S. Pat. Nos. 4,061,724 and 4,073,865, the disclosures of which are incorporated herein by reference. Other molecular sieves useful in this invention include crystalline microporous molecular sieve oxides that are based on the presence of aluminophosphate in the framework of the crystal structures, e.g., those commonly known by the acronyms SAPO, MeAPO, FAPO, MAPO, MnAPO, CoAPO, ZAPO, MeAPSO, FAPSO, MAPSO, MnAPSO, CoAPSO, ZAPSO, ElAPO, ElAPSO and the like, including mixtures thereof. Such molecular sieves are described, for example, in U.S. Pat. Nos. 4,567,029, 4,440, 871, 4,500,651, 4,554,143 and 4,310,440, the disclosures of which are incorporated herein by reference.

The zeolites and molecular sieves preferably have a pore size greater than about 5 Angstrom units and less than about 10 Angstrom units, preferably between about 5.2 and about 8 Angstrom units, and more preferably between about 5.5 and about 6.5 Angstrom units. Of course the zeolites and molecular sieves may contain meso- and macro-pores along with the preferred pore sizes. Mixtures of zeolites and molecular sieves may be employed in the processes of this invention. Illustrative of suitable zeolites and molecular sieves include those permissible zeolites and molecular sieve materials described in "Zeolite, Clay, and Heteropoly Acid in Organic Reactions", by Yusuke Izumi, Kazuo Urabe and Makato Onaka, VCH Publishers Inc., 1992, supra.

As indicated above, the catalysts and catalytic components of this invention may be utilized with or without support. However, when a support is employed, the catalyst can be produced by depositing the catalytic components on the support either separately or in combination. The support can be selected from the group of silica, gamma alumina, titania, zirconia, alumina silicates, clays, and activated carbon, although other supports may be used. As described herein, certain supports such as clays may also be employed as the alcohol carbonylation catalyst or catalytic component. Mixed composite supports in which a high surface area support is deposited over a lower surface area support may also be used. The surface area of the support does not appear to be critical to obtaining the benefits of this invention; thus, supports within a wide range of surface areas, e.g., at least about 1 square meter per gram or higher (as determined by BET) should suffice.

The catalyst may be present in the reactor in any of a variety of forms. It may be present as a physical admixture or blend of each of the catalytic components, a uniform catalyst prepared by known co-precipitation techniques, continuous or discontinuous portions or layers of the different components impregnated into or coated on a support, or as staggered, alternating or, simply, distinct portions of the different components placed within the reactor.

Conventional impregnation procedures can be used in instances in which the catalyst is impregnated into a support. The impregnation process can be as simple as contacting the support with a solution containing both components or separate solutions each containing one component, followed by heating the coated support to a temperature and for a period of time in which the solvent(s) is(are) removed but which does not significantly adversely affect the catalytic activity of the catalytic component(s). Typically, such temperatures may range from about 100° C. to about 900° C. for a period of time ranging from a few seconds up to about 8 hours or more. Alternatively, precipitation of one or more of the components either in combination or separately may be useful in preparing supported catalysts. The precipitation can be accomplished either on the support surface or in the pores. Such precipitation may be carried out by conventional methods.

The use of heterogeneous alcohol carbonylation catalysts or alcohol carbonylation catalytic components as described herein permits the reaction to proceed without the addition of an iodide promoter, such as $CH_3I$ and/or HI which are highly corrosive, necessitate the use of expensive corrosion resistant materials of construction and require extensive separation procedures to remove the iodide from the product stream.

For the multicomponent catalysts of this invention, the weight ratio of the alcohol synthesis catalytic component to the alcohol carbonylation catalytic component present in the catalyst should be such that the desired product stream is produced. The weight ratio may vary from about 50:1 to 1:50, with an especially preferred weight ratio of these catalytic components being about 10:1 to 1:10. The specific ratio selected will depend upon such factors as the activity and selectivity of each catalytic component, the reaction conditions, the desired product stream composition, etc. and can readily be determined by one skilled in the art from routine experimentation from the teachings provided herein.

The processes and catalysts of this invention enable the production of oxygenates at desirable reaction rates. In the embodiment which employs a multicomponent catalyst in a single reaction zone, the catalyst components can be varied so as to control reaction rates. In the embodiment which employs an alcohol synthesis catalyst in a first reaction vessel and a carbonylation catalyst in a second reaction vessel, the two catalysts can be varied so as to control reaction rates. Reaction rates are not narrowly critical and preferably are at least about 0.5 pounds of product per cubic foot of catalyst per hour (0.5 lb/ft3 cat/hr) and more preferably at least about 1.0 lb/ft3 cat/hr. The particular reaction rates will be governed by the best compromise between achieving high catalyst selectivity, lifetime and ease of operability, as well as the intrinsic reactivity of the starting materials and the stability of the starting materials and the desired reaction product to the reaction conditions.

Further, the processes and catalysts of this invention enable the production of oxygenates at desirable selectivities. In the embodiment which employs a multicomponent catalyst in a single reaction zone, the catalyst components can be varied so as to control product selectivities. In the embodiment which employs an alcohol synthesis catalyst in a first reaction vessel and a carbonylation catalyst in a second reaction vessel, the two catalysts can be varied so as to control product selectivities. Product selectivities are not narrowly critical and preferably are at least about 25 percent and more preferably at least about 50 percent of the desired product. The particular selectivities will be governed by the best compromise between achieving high catalyst activity, lifetime and ease of operability, as well as the intrinsic reactivity of the starting materials and the stability of the starting materials and the desired reaction product to the reaction conditions.

Recovery and purification of desired products may be accomplished by any appropriate means. The desired products of this invention may be recovered in any conventional manner and one or more separators or separation zones may be employed in any given process to recover the desired reaction product from its crude reaction product. Suitable separation and purification methods include, for example, distillation, phase separation, extraction, absorption, crystallization, membrane, derivative formation and the like.

As described herein, the processes of this invention may involve one or more recycle procedures. Gas and/or liquid recycle procedures may be employed as appropriate. For example, as depicted in FIG. 1, the gaseous and liquid residuals are removed from the refining unit 12 via line 16 and recycled to the reactor 8 via lines 16 and 18 and/or to the reformer unit 4 via lines 16 and 20. Also, as depicted in FIG. 2, the gaseous and liquid residuals are removed from the refining unit 13 via line 16 and recycled to the reactor 8 via lines 16 and 18 and/or to the reformer unit 4 via lines 16 and 20.

The following more detailed description of preferred embodiments of this invention, the production of acetic acid in a one-reactor and two-reactor processes, is not intended to limit the scope of the invention in any respect as the processes and catalysts may be utilized for the manufacture of other acids, esters, anhydrides and mixtures thereof using the concepts heretofore and hereafter fully and adequately disclosed.

In FIG. 1, which is a simplified flow diagram of an embodiment of this invention, a one-reactor process for the preparation of acetic acid from a hydrocarbon feed stream is shown. The hydrocarbon feed stream is supplied to a synthesis gas generation unit, 4, via line 2 wherein a synthesis gas comprising a mixture of hydrogen and carbon monoxide is generated and provides the feedstock to the reactor. The feedstock gas exits the synthesis gas generation unit via line 6 and enters the reactor 8. The reactor, containing a catalyst comprising an alcohol synthesis catalytic component and an alcohol carbonylation catalytic component, is maintained at pre-selected reaction conditions of temperature and pressure so that a vapor phase reaction takes place in which the feedstock gas is converted to oxygenates, most preferably containing a large fraction of acetic acid. The product stream, in gaseous form, exits the reactor 8 via line 10 and enters a refining unit 12, wherein the product stream is condensed to form a gas phase and a liquid phase. The refining unit is controlled so that a product stream consisting essentially of acetic acid is removed from the refining unit via line 14 and recovered essentially free of esters, anhydrides, and mixtures thereof The gaseous and liquid residuals are removed from the refining unit via line 16 and recycled to the reactor 8 via lines 16 and 18 and/or to the reformer unit 4 via lines 16 and 20.

Figure 2:
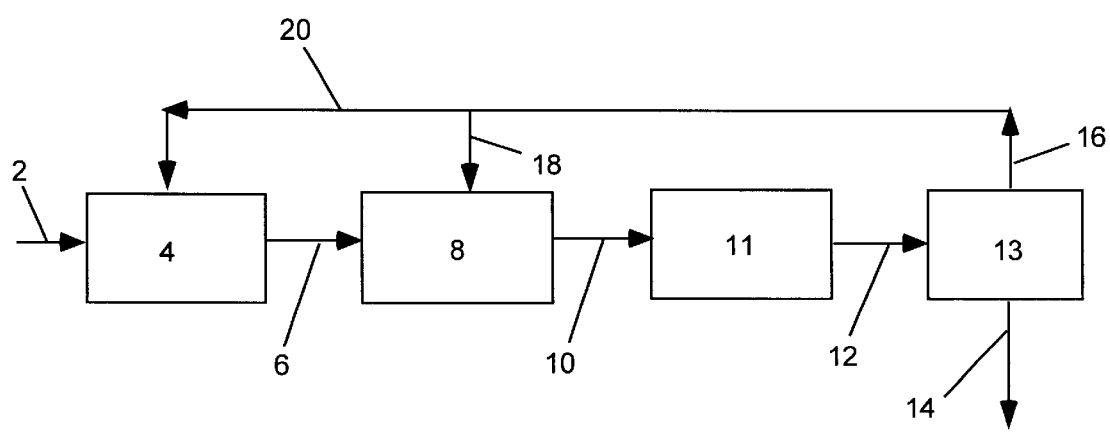
FIG. 2 is a schematic representation of a two-reactor process flow diagram to make acetic acid from a feedstock gaseous mixture comprising carbon monoxide and hydrogen gases prepared from a hydrocarbon feed to a "synthesis gas" or "syn gas" generator.

In FIG. 2, which is a simplified flow diagram of an embodiment of this invention, a two-reactor process for the preparation of acetic acid from a hydrocarbon feed stream is shown. A hydrocarbon feed stream is supplied to a synthesis gas generation unit, 4, via line 2 wherein a synthesis gas comprising a mixture of hydrogen and carbon monoxide is generated and provides the feedstock to the alcohol synthesis reactor. The feedstock gas exits the synthesis gas generation unit via line 6 and enters the alcohol synthesis reactor 8. The alcohol synthesis reactor, containing an alcohol synthesis catalyst is maintained at pre-selected reaction conditions of temperature and pressure so that a vapor phase reaction takes place in which the feedstock gas is converted to an alcohol-containing stream, most preferably containing a large fraction of methanol or dimethyl ether. The product stream, in gaseous form, exits the reactor 8 via line 10 and enters a carbonylation reactor 11. The carbonylation reactor, containing an alcohol carbonylation catalyst, is maintained at pre-selected reaction conditions of temperature and pressure so that a vapor phase reaction takes place in which the alcohol-containing feedstock is converted to oxygenates, most preferably containing a large fraction of acetic acid or methyl acetate. The product stream, in gaseous form, exits the reactor 11 via line 12 and enters a refining unit 13, wherein the product stream is condensed to form a gas phase and a liquid phase. The refining unit may be controlled so that a product stream consisting essentially of acetic acid is removed from the refining unit via line 14 and recovered essentially free of esters, anhydrides, and mixtures thereof The gaseous and liquid residuals are removed from the refining unit via line 16 and recycled to the reactor 8 via lines 16 and 18 and/or to the reformer unit 4 via lines 16 and 20.

As shown in FIG. 2, the carbonylation reaction can be carried out by passing the substrate to be carbonylated and synthesis gas over the catalyst as a vapor phase reaction or as a liquid phase reaction, e.g., a slurry reaction. As shown in FIG. 2, methanol can be formed in situ by feeding synthesis gas to a methanol producing catalyst that is coupled to the carbonylation catalyst either in the same or different reactors. If desired, either methanol, synthesis gas or both can be obtained from a different source and fed directly to the carbonylation catalyst.

The reactors described with reference to FIGS. 1 and 2 may be a tube and shell design reactors, wherein the catalyst is a fixed bed catalyst and the reaction takes place in the vapor phase. Other types of reactions and, correspondingly, reactors that can be used include a fluidized bed, where the solid catalyst system is fluidized by the incoming gas stream, a slurry reactor where the catalyst is insoluble in the reaction media, or a bubble column reactor. When acetic acid is the desired product, it will be the most corrosive component in the reactor so the material of construction for the reactor need only be stainless steel, a relatively inexpensive material as compared to the exotic materials, such as Hastelloy C or zirconium clad Hastelloy, used in commercial processes employing a homogeneous iodide-promoter.

From the above description, it should be readily apparent that the reactor and refining section are highly simplified when a vapor phase reaction is utilized because there is no liquid recycle of the catalyst system. Moreover, because iodide promoters are not needed for this invention, apparatus to recover the highly corrosive iodide from the product stream can be eliminated.

One embodiment of this invention provides an integrated conversion which permits the use of a single reactor constructed of lower cost materials to convert, in the presence of a unique multi-component catalyst, a feedstock comprising hydrogen and carbon monoxide to, most preferably, acetic acid under uniform temperature and pressure processing conditions. While specific reference in describing the FIG. 1 has been made to the manufacture of acetic acid, this invention, as described heretofore, is capable of producing any of a variety and/or combination of oxygenates. A plurality of dual catalyst bed reactors may employed in the practice of this invention. Likewise, a plurality of separate reactors for steps (a) and (b) described above may employed in any permissible combination.

The processes of this invention may be carried out using, for example, a fixed bed reactor, a fluid bed reactor, a continuous stirred tank reactor (CSTR) or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the materials present during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials.

When complete conversion is not desired or not obtainable, the starting materials can be separated from the product and the starting materials then recycled back into the reaction zone.

For purposes of this invention, the chemical elements are identified in accordance with the Periodic Table of the Elements reproduced in "Hawley's Condensed Chemical Dictionary" 12th Edition, Revised by Richard J. Lewis, Sr., Van Nostrand Reinhold Company, New York, 1993.

The following examples are intended to demonstrate the unexpected advantages, uniqueness and superiority of the invention as compared to the prior art.

EXAMPLE 1

The reaction system consists of a feed system, a fixed bed reactor, and an on-line analyzer. The system is capable of high temperature and high pressure operation. In the feed system, a synthesis gas feedstock is first passed through an activated carbon trap to remove metal carbonyl contaminants. The purified feedstock then passes through a mass flow meter and into the reaction tube inlet. The reaction tube is stainless steel and is heated with an air fluidized sand bath. The gas product stream exiting the reactor enters into an analytical section equipped with switching valves that provide 0.6 milliliter reactor off-gas samples that are analyzed in a Varian 3700 gas chromatograph equipped with two detectors. $H_2$, $N_2$, CO and $CO_2$ are separated on a 10', $\frac{1}{8}$", $^{80}/_{100}$ Carbosieve S-2 column purchased from Supelco and detected by thermal conductivity. All organic products are resolved on a 12', $\frac{1}{8}$", $^{80}/_{100}$ Tenax column obtained from Alltech and detected using flame ionization. Argon is used as the carrier gas for both columns.

A reactor tube was first charged with quartz beads followed by 1.0 gram of a Cu—Zn oxide methanol synthesis catalytic component (United Catalyst No. 2537-S) that was bulk mixed with 2 grams of quartz beads. This catalytic component was reduced at 270° C. in a 5%$H_2$/95%$N_2$ stream for 6 hours.

As the heterogeneous alcohol carbonylation catalytic component an iridium and palladium exchanged $H_3W_{12}PO_{40}$ heteropoly acid catalytic component was used. The component was prepared by the procedure described in U.S. Pat. No. 5,330,955, as follows:

$Pd(NO_3)_2$ (0.23 grams) and $IrCl_3.3H_2O$ (0.37 grams) were added to 50 milliliters of degassed methanol under $N_2$ in a Schlenk flask and stirred for 0.5 hour. Next, $H_3W_{12}PO_{40}$ (6.50 grams) was added and the mixture was stirred for an additional 1 hour. Activated Grade 12 silica gel ($SiO_2$) was added and the slurry stirred for 4 hours. The methanol was then removed at 80° C., under vacuum, yielding Ir—Pd—$H_3W_{12}PO_{40}$—$SiO_2$. This catalytic component has essentially the same composition reported for Example 17 of U.S. Pat. No. 5,330,955, where the mole ratio of M1:M2:$H_3W_{12}PO_{40}$ is approximately 1:1:2 with MI being iridium and M2 being palladium.

The reactor tube was opened and 2.069 grams of Ir—Pd—$H_3W_{12}PO_{40}$—$SiO_2$ mixed with 2 grams of quartz beads was added to Cu—Zn oxide methanol catalytic component in the reactor. The reactor tube was then connected to the reaction system and the entire system flushed with nitrogen. The reactor bed was packed in such a way that the incoming synthesis gas first contacted the Cu—Zn catalytic component, and then the reaction stream contacted the Ir—Pd—$H_3W_{12}PO_{40}$—$SiO_2$.

The reaction zone was maintained at a uniform temperature of about 235° C. and a uniform pressure of about 1000 psig with the synthesis gas having a hydrogen to carbon monoxide molar ratio of 1:1. The GHSV of the syn gas fed to the reactor was 6000/hr. After 16 hours of reaction a sample of the reaction menstruum was analyzed. The analysis showed the carbon monoxide conversion was about 5% and the reaction product distribution was $CH_4$=15.1%, $C_2H_6$=4.1%, $CH_3OH$=62.1%, and $CH_3COOH$=17.5%.

The catalyst was relatively stable over the test period of 168 hours. The stability of the catalyst was surprising because the heterogeneous alcohol carbonylation catalytic compound significantly deactivated after 8 hours when only methanol and carbon monoxide were fed to the reactor. The presence of hydrogen and carbon monoxide in the reactor appears to be the reason for the unexpected increase in the stability of the heterogeneous alcohol carbonylation catalytic component of the catalyst.

EXAMPLE 2

A Ir—Pd—$H_3W_{12}PO_{40}$-Carbon catalyst was prepared as follows. $Pd(NO_3)_2$ (0.23 grams) and $IrCl_3.3H_2O$ (0.37 grams) were added to 50 milliliters of degassed methanol under $N_2$ in a Schlenk flask and stirred for 0.5 hour. Next, $H_3W_{12}PO_{40}$ (6.50 grams) was added and the mixture was stirred for an additional 1 hour. Activated Carbon (3.90 grams, Calgon 35–100 mesh) was added and the slurry stirred for 4 hours. The methanol was evaporated and Ir—Pd—$H_3W_{12}PO40$-Carbon was recovered.

2.002 grams of Ir—Pd—$H_3W_{12}PO_{40}$-Carbon was charged to the reactor as described in Example 1 and the reaction was carried out similar to Example 1 at 235° C. and 1000 psig with $H_2$:CO=1:1. After 16 hours of reaction a sample of the reaction menstruum was analyzed. The analysis showed the carbon monoxide conversion was about 7% and the product distribution was $CH_4$=45.4%, $C_2H_6$=7.7%, $CH_3OH$=30.1%, and $CH_3COOH$=13.1%.

EXAMPLE 3

A Ir—Pd—Cs—$H_3W_{12}PO_{40}$ catalyst was prepared as follows. $Pd(NO_3)_2$ (0.23 grams) and $IrCl_3.3H_2O$ (0.37 grams) were added to 50 milliliters of degassed methanol under $N_2$ in a Schlenk flask and stirred for 0.5 hour. Next, $H_3W_{12}PO_{40}$ (6.50 grams) was added and the mixture was stirred for an additional 4 hours. After this time $CsCO_3$ (0.67 grams) was added and within 2 minutes a precipitate formed. This mixture was stirred for 16 hours after which the methanol was removed by vacuum and a gray powder (Ir—Pd—Cs—$H_3W_{12}PO_{40}$) was recovered.

2.001 grams of Ir—Pd—Cs—$H_3W_{12}PO_{40}$ was charged to the reactor, in the absence of a support, as described in Example 1 and the reaction was carried out similar to Example 1 at 235° C. and 1000 psig with $H_2$:CO=1:1. After 16 hours of reaction a sample of the reaction menstruum was analyzed. The analysis showed the carbon monoxide conversion was about 6% and the product distribution was $CH_4$=32.8%, $C_2H_6$=4.4%, $CH_3OH$=45.1%, and $CH_3COOH$=15.9%.

EXAMPLE 4

A Ru—$H_3W_{12}PO_{40}$—$SiO_2$ catalyst was prepared as follows. $RuCl_3$ (0.27 grams) was dissolved in 50 milliliters of degassed methanol. Next, $H_3W_{12}PO_{40}$ (6.50 grams) was added and the mixture was stirred for an additional 4 hours. $SiO_2$ (3.90 grams, Grade 15) was added and the slurry stirred for 4 hours. The methanol was evaporated and Ru—$H_3W_{12}PO_{40}$—$SiO_2$ was recovered.

2.001 grams of Ru—$H_3W_{12}PO_{40}$—$SiO_2$ was charged to the reactor as described in Example 1 and the reaction was carried out similar to Example 1 at 235° C. and 1000 psig with $H_2$:CO=1:1. After 16 hours of reaction a sample of the reaction menstruum was analyzed. The analysis showed the carbon monoxide conversion was about 5% and the product distribution was $CH_4$=13.2%, $C_2H_6$ and $C_3H_8$=10%, $CH_3OH$=55.1%, and $CH_3COOH$=21.1%.

EXAMPLE 5

A Ru—$H_3W_{12}PO_{40}$-Carbon catalyst was prepared as described in Example 4 except 3.90 grams of activated carbon was used instead of silica. 2.003 grams of Ru—$H_3W_{12}PO_{40}$-Carbon was charged to the reactor as described in Example 1 and the reaction was carried out similar to Example 1 at 235° C. and 1000 psig with $H_2$:CO=1:1. After 16 hours of reaction a sample of the reaction menstruum was analyzed. The analysis showed the carbon monoxide conversion was about 6% and the product distribution was $CH_4$=32.6%, $C_2H_6$ and $C_3H_8$=6.2%, $CH_3OH$=45.1%, and $CH_3COOH$=15.9%.

EXAMPLE 6

A Rh—$H_3W_{12}PO_{40}$—$SiO_2$ catalyst was prepared as follows. $RhCl_3.3HO$ (0.28 grams) was dissolved in 50 milliliters of degassed methanol. Next, $H_3W_{12}PO_{40}$ (6.50 grams) was added and the mixture was stirred for an additional 4 hour. SiO (3.90 grams, Grade 15) was added and the slurry stirred for 4 hours. The methanol was evaporated and Rh—$H_3W_{12}PO_{40}$—$SiO_2$ was recovered.

2.000 grams of Rh—$H_3W_{12}PO_{40}$—$SiO_2$ was charged to the reactor as described in Example 1 and the reaction was carried out similar to Example 1 at 235° C. and 1000 psig with $H_2$:CO=1:1. After 16 hours of reaction a sample of the reaction menstruum was analyzed. The analysis showed the carbon monoxide conversion was about 7.2% and the product distribution was $CH_4$=22.8%, $C_2H_6$ and $C_3H_8$=20.1%, $CH_3OH$=36.1%, and $CH_3COOH$=17.1%.

EXAMPLE 7

A RH—$H_3W_{12}PO_{40}$-carbon catalyst was prepared as described in Example 6 except 3.90 grams of activated carbon was used instead of silica. 2.01 grams of Rh—$H_3W_{12}PO_{40}$-carbon was charged to the reactor and the reaction was carried out similar to Example 1 at 235° C. and 1000 psig with $H_2$:CO=1:1. After 16 hours of reaction a sample of the reaction menstruum was analyzed. The analysis showed the carbon monoxide conversion was about 6.5% and the product distribution was $CH_4$=15.9%, $C_2H_6$ and $C_3H_8$=12.1%, $CH_3OH$=53.2%, and $CH_3COOH$=18.7%.

EXAMPLE 8

Preparation of $ZrO_2$—$WO_3$ Solid Super Acid 82.3 grams of $ZrOCl_2.8H_2O$ were dissolved in 1 liter of distilled $H_2O$ giving a clear solution. 30% ammonium hydroxide was added drop wise until the pH remained >9. Addition of the hydroxide results in the immediate hydrolysis of $ZrOCl_2.8H_2O$ to $Zr(OH)_4$ and formation of a slurry. The slurry was stirred for about ½ hr and then filtered to recover the $Zr(OH)_4$. This gel-like material was dried at 120° C. for 16 hours and yielded 32.5 grams of a white granular solid that was crushed into a powder.

5.014 grams of $Zr(OH)_4$ powder were placed in a 50 milliliter beaker. The $Zr(OH)_4$ was impregnated via incipient wetness with 1.2204 grams of $(NH_4)_6H_2W_{12}O_{40}$ dissolved in 10 milliliters of distilled $H_2O$. The wet solid was dried at 120° C. and then calcined at 800° C. in static air for 4 hours. 5.471 grams of a lemon yellow powder were obtained. This material is considered to be the solid super acid $ZrO_2$—$WO_3$ with an empirical $WO_3$ loading of 23 wt %.

EXAMPLE 9

Preparation of $TiO_2$—$WO_3$ Solid Super Acid 30 milliliters of Ti(isopropyl)$_4$ was added dropwise to 500 milliliters of deionized water at room temperature over 30 minutes. The slurry was stirred for 1 hour, filtered, air dried, and then placed in an oven to dry at 120° C. for 16 hours. 8.834 grams of hydrated $TiO_2$ was obtained. This powder was impregnated with 1.9068 grams of $(NH_4)_6H_2W_{12}O_{40}$ dissolved in 15 milliliters of distilled $H_2O$. The damp mixture was well stirred, air dried for 1 hour, and then placed in an oven to dry at 120° C. for 16 hours. The mixture was then calcined at 800° C. for 4 hours from which 9.85 grams of a lemon yellow solid was obtained. This material is considered to be the solid super acid $TiO_2$—$WO_3$ with an empirical $WO_3$ loading of 23 wt %.

EXAMPLE 10

Preparation of $HfO_2$—$WO_3$ Solid Super Acid $HfO_2$—$WO_3$ was prepared essentially the same as $ZrO_2$—$WO_3$. 50.0 grams of $HfOCl_2.8H_2O$ were dissolved in 0.5 liter of distilled $H_2O$ giving a clear solution. 30% ammonium hydroxide was added dropwise, with rapid stirring, until a pH of about 10 was obtained. The slurry was mixed for 5 minutes, then was filtered to recover the $Hf(OH)_4$. The Hf(OH)4 was washed with 3 liters of distilled $H_2O$ and the gelatinous material was dried at 120° C. for 16 hours. The resulting white, granular material was then crushed into a powder.

7.0 grams of $Hf(OH)_4$ was impregnated via incipient wetness with 1.0 grams of $(NH_4)_6H_2W_{12}O_{40}$ dissolved in 3 milliliters of distilled $H_2O$. The wet solid was dried at 120° C. and then calcined at 700° C. in static air for 3.5 hours to produce a green powder. This material is considered to be the solid super acid $HfO_2$—$WO_3$ with an empirical $WO_3$ loading of 13.5 wt %.

EXAMPLE 11

Preparation of Ir—$ZrO_2$—$WO_3$ $ZrO_2$—$WO_3$ was impregnated with Ir by incipient wetness. A variety of soluble Ir compounds can be used. For example, 0.0379 grams of $IrCl_3.3H_2O$ were dissolved in 3 milliliters of distilled $H_2O$. This solution was added drop wise with stirring to 2.0651 grams of $ZrO_2$—$WO_3$. Once the solid became damp addition of Ir was stopped and the solid was dried at 120° C. This procedure was repeated until all the Ir solution was utilized. The material was dried for 16 hours at 120° C. yielding 2.0365 grams of a yellow-tan solid. This material is considered to be Ir(1)—$ZrO_2$—$WO_3$(23) where (1) indicates the Ir metal loading in wt % metal basis.

EXAMPLE 12

Preparation of Pd—$ZrO_2$—$WO_3$ $ZrO_2$—$WO_3$ was impregnated with Pd by incipient wetness. A variety of soluble Pd compounds can be used. For example, 0.0026 grams of $Pd(NO_3)_2 \cdot H_2O$ were dissolved in 4.0 milliliters of distilled $H_2O$ and was added drop wise with stirring to 4.0 grams of $ZrO_2$—$WO_3$. Once the solid became damp addition of Pd was stopped and the solid was dried at 120° C. This procedure was repeated until all the Pd solution was utilized. The material was dried for 16 hours at 120° C. to produce a bright yellow powder. This material is considered to be $Pd(0.02)$—$ZrO_2$—$WO_3(18)$ where (0.02) indicates the Pd metal loading in wt % metal basis.

EXAMPLES 13–19

For the following examples, the reactions were carried out in a ⅜"316 stainless steel reactor tube capable of high pressure operation. The reactor was housed in a convection oven. Synthesis gas was supplied to the reactor under pressure, as was any liquid feed. The product stream exiting the reactor was maintained as a vapor and sent to an online GC for analysis. Regarding reactor tube loading, a reactor tube was first charged with quartz beads followed by 2 to 3 grams of the carbonylation catalyst mixed with 2 grams of quartz beads. The reactor tube was then connected to the reaction system and the entire system was well flushed with nitrogen. The gas feed was switched to synthesis gas and the reaction system brought to operating conditions. Liquid feed, if used, was then added. In the case of coupling a methanol catalyst with the carbonylation catalyst, the reactor was first packed with the methanol catalyst and then packed with the carbonylation catalyst. Synthesis gas first contacted the methanol catalyst and that product stream then contacted the carbonylation catalyst. Table A below contains data for various catalysts prepared as described above used to carbonylate methanol to methyl acetate or a mixture of methyl acetate and acetic acid. For all examples, the reaction was carried out at 1000 psig with 1:1 $H_2$:CO gas feed. Methanol was fed to the reactor as a neat liquid at the reported LHSV. The results are set forth in Table A. The amounts (in parenthesis) of catalyst composition components set out in Table A are given as weight percents.

TABLE A

| Catalyst | Pd (0.5)-$ZrO_2$-$WO_3$ (23) | Pd (0.5)-$ZrO_2$-$WO_3$ (23) | Pd (0.02)-$ZrO_2$-$WO_3$ (18) | Pt (0.04)-$ZrO_2$-$WO_3$ (18) | Ir (0.04)-$ZrO_2$-$WO_3$ (18) | Ir(0.02)-Pd(0.02)-$ZrO_2$-$WO_3$ (23) | Pd (0.1)-$ZrO_2$-$MoO_3$ (12) |
|---|---|---|---|---|---|---|---|
| Temperature, ° C. | 320 | 330 | 300 | 300 | 300 | 300 | 300 |
| Feed, mole % | | | | | | | |
| $H_2$ | 43.45 | 47.8 | 45.4 | 45.4 | 45.4 | 45.4 | 45.4 |
| CO | 43.45 | 47.8 | 45.4 | 45.4 | 45.4 | 45.4 | 45.4 |
| methanol | 13.1 | 4.3 | 9.5 | 9.5 | 9.5 | 9.5 | 9.5 |
| Inlet GHSV, $hr^{-1}$ | 12000 | 12000 | 9500 | 9500 | 9500 | 9500 | 9500 |
| Inlet LHSV, $hr^{-1}$ | 1.5 | 0.45 | 1.5 | 1.5 | 1.5 | 1.5 | 1.5 |
| Product stream, mole % | | | | | | | |
| dimethyl ether | 24.2 | 11.3 | 59.3 | 57.9 | 58.1 | 57.6 | 5.1 |
| methanol | 21.6 | 16.8 | 27.6 | 25.6 | 27.5 | 27.4 | 56.1 |
| methyl acetate | 25.1 | 8.5 | 7.1 | 7.2 | 8.1 | 7.3 | 7.7 |
| acetic acid | 8.8 | 28.5 | 0 | 0 | 0 | 0 | 0 |
| methane | 18.2 | 25.7 | 1.5 | 4.5 | 1.7 | 3.2 | 27.8 |
| carbon dioxide | 1.5 | 7.0 | 4.2 | 4.5 | 4.3 | 3.9 | 2.1 |
| Rate, lb/ft³cat/hr | | | | | | | |
| acetic acid | 9.3 | 10.2 | 0 | 0 | 0 | 0 | 0 |
| methyl acetate | 32.4 | 3.8 | 7.3 | 7.4 | 8.1 | 7.6 | 11.4 |
| MeOH conversion, % | 47.3 | 66.2 | 12.7 | 15.1 | 15.2 | 13.6 | 41.2 |
| CO conversion, % | 12.0 | 6.4 | 4.1 | 4.2 | 4.2 | 5.1 | 3.1 |

EXAMPLES 20–22

Various liquid feeds were carbonylated and the results are given in Table B below. The reactions were carried out similarly to Examples 13–19. The results listed in column 1 demonstrate that dimethyl ether is readily carbonylated to methyl acetate. The other results indicate that mixtures of methyl acetate and methanol are carbonylated. These results are important with respect to mixtures of methanol, dimethyl ether, and methyl acetate being recycled back to the reactor. The amounts (in parenthesis) of catalyst composition components set out in Table B are given as weight percents.

TABLE B

| Catalyst | Ir(0.1)-$ZrO_2$—$WO_3$(18) | Pd(0.1)-$ZrO_2$—$WO_3$(23) | Pd(0.1)-$ZrO_2$—$WO_3$(23) |
|---|---|---|---|
| Temperature, ° C. | 300 | 325 | 315 |
| Pressure, psig | 1000 | 1000 | 1000 |
| Feed, mole % | | | |
| $H_2$ | 48.4 | 47.9 | 46.2 |
| CO | 48.4 | 47.9 | 46.2 |
| methanol | 0 | 1.0 | 5.7 |
| methyl acetate | 0 | 3.2 | 1.9 |
| dimethyl ether | 3.2 | 0 | 0 |
| Inlet GHSV, $hr^{-1}$ | 9000 | 11000 | 8200 |

TABLE B-continued

| Catalyst | Ir(0.1)-ZrO$_2$—WO$_3$(18) | Pd(0.1)-ZrO$_2$—WO$_3$(23) | Pd(0.1)-ZrO$_2$—WO$_3$(23) |
|---|---|---|---|
| Inlet LHSV, hr$^{-1}$ | 0.75 | 1.36 | 1.36 |
| Product stream, mole % | | | |
| dimethyl ether | 58.6 | 14.7 | 23.1 |
| methanol | 14.2 | 17.5 | 19.0 |
| methyl acetate | 13.1 | 39.5 | 36.6 |
| acetic acid | 2.5 | 9.9 | 7.8 |
| methane | 9.1 | 12.2 | 11.7 |
| carbon dioxide | 1.2 | 2.7 | 1.3 |
| Rate, lb/ft$^3$cat/hr | | | |
| acetic acid | 1.2 | 8.45 | 6.3 |
| methyl acetate | 7.4 | — | — |
| Methanol conversion, % | — | 72.3 | 61.2 |
| CO conversion, % | 12.0 | 8.2 | 13.7 |

EXAMPLES 23–26

In the following examples, the reactor tube was first packed with a Cu—Zn methanol producing catalyst followed by one of the catalysts listed in Table C below. The tube was placed in an oven and synthesis gas was passed through the tube contacting the methanol catalyst first. The gas mixture then passed through the carbonylation catalyst. The temperature and pressure were the same for both catalysts. In no case was a liquid fed to the reactor. The results demonstrate that the carbonylation catalyst can be coupled to a methanol producing catalyst and that various Group 7, 8, 9, 10 and/or 11 metals form active catalysts. The results are set forth in Table C. The amounts (in parenthesis) of catalyst composition components set out in Table C are given as weight percents.

TABLE C

| Catalyst | Ir(1.0)-TiO$_2$—WO$_3$(23) | Rh(0.1)-ZrO$_2$—WO$_3$(20) | Re(1.0)-ZrO$_2$—WO$_3$(23) | Cs(1.0)-ZrO$_2$—WO$_3$(23) |
|---|---|---|---|---|
| Temperature, °C. | 275 | 300 | 300 | 275 |
| Pressure, psig | 1000 | 1000 | 1000 | 1000 |
| Feed, mole % | | | | |
| H$_2$ | 50 | 50 | 50 | 50 |
| CO | 50 | 50 | 50 | 50 |
| Inlet GHSV, hr$^{-1}$ | 6300 | 7900 | 6000 | 6000 |
| Product stream, mole % | | | | |
| dimethyl ether | 38.2 | 28.2 | 23.6 | 61.7 |
| methanol | 46.4 | 17.7 | 20.7 | 21.6 |
| methyl acetate | 1.8 | 5.5 | 3.5 | 1.9 |
| acetic acid | 0.1 | 0 | 0.4 | 0.1 |
| methane | 2.7 | 9.2 | 4.2 | 1.9 |
| carbon dioxide | 10.0 | 33.2 | 42.3 | 11.4 |
| Rate, lb/ft$^3$cat/hr | | | | |
| acetic acid | 0.1 | 0 | 0.2 | 0.1 |
| methyl acetate | 1.1 | 4.7 | 2.9 | 1.1 |

EXAMPLES 27–31

In each of these examples, methanol was carbonylated to a mixture of methyl acetate and acetic acid. The results are given in Table D below. The reactions were carried out in a manner similar to Examples 13–19. The results demonstrate that Group 10 and 11 metals impregnated onto catalysts containing tungsten oxide and zirconium oxide are useful in this invention.

TABLE D

| Example | Catalyst | Temp, °C. | Pressure, psi | Carbonylation Rate lb/ft3 cat-hr* |
|---|---|---|---|---|
| 27 | Ag$_{0.6}$—ZrO$_2$—WO$_3$ | 300 | 1000 | 3.6 |
| 28 | Ag$_{0.25}$—ZrO$_2$—WO$_3$ | 325 | 1000 | 10.3 |
| 29 | Cu$_{0.5}$—ZrO$_2$—WO$_3$ | 300 | 1000 | 3.3 |
| 30 | Pt$_{0.05}$—Al$_2$O$_3$ mixed with ZrO$_2$—WO$_3$ | 300 | 1000 | 3.1 |

TABLE D-continued

| Example | Catalyst | Temp, °C. | Pressure, psi | Carbonylation Rate lb/ft3 cat-hr* |
|---|---|---|---|---|
| 31 | $Pd_{5.0}$—$SiO2$ mixed with $ZrO_2$—$WO_3$ | 300 | 1000 | 1.1 |

*Carbonylation rate is defined as acetic acid + acetic acid equivalents in methyl acetate.

EXAMPLES 32–46

In each of these examples, methanol was carbonylated to a mixture of methyl acetate and acetic acid. The results are given in Table E below. The reactions were carried out in a manner similar to Examples 13–19. All examples were run at a pressure of 1000 psig, a $H_2$:CO ratio of 1:1, and the alcohol synthesis catalyst was United Catalyst No. 2537-S. The results demonstrate that clays may be effectively used as the alcohol carbonylation catalyst.

TABLE E

| Catalyst | °C. | GHSV $hr^{-1}$ 1st Stage | GHSV $hr^{-1}$ 2nd Stage | Productivity, lbs/$ft^3$cat/hr HOAc | Productivity, lbs/$ft^3$cat/hr MeOAc | Total HC |
|---|---|---|---|---|---|---|
| Montmorillonite | | | | | | |
| $H^+$ | 300 | 6000 | 3000 | 0.08 | 0.10 | 0.98 |
| $Al^{+3}$ | 300 | 6000 | 3000 | 0.04 | 0.08 | 0.63 |
| Ir—$Al^{+3}$ | 300 | 6000 | 3000 | 0.05 | 0.47 | 1.44 |
| $Fe^{+3}$-pillared | 300 | 6000 | 3000 | 0.05 | 0.09 | 0.95 |
| Ir—$Fe^{+3}$-pillared | 250 | 6000 | 3000 | 0.02 | 0.27 | 0.65 |
| Ir—$Fe^{+3}$-pillared | 300 | 6000 | 3000 | 0.05 | 3.21 | 6.53 |
| Bentonite | | | | | | |
| $H^+$ | 300 | 6000 | 3000 | 0.04 | 0.04 | 0.46 |
| Ir—$Al^{+3}$ | 300 | 6000 | 3000 | 0.31 | 0.14 | 1.62 |
| Ir—$Fe^{+3}$ | 300 | 6000 | 3000 | 0.09 | 0.05 | 1.26 |
| Ir—$Al^{+3}$-pillared | 300 | 6000 | 3000 | 0.87 | 0.10 | 1.21 |
| Ir—$Fe^{+3}$-pillared | 300 | 6000 | 3000 | 0.15 | 0.11 | 1.23 |
| Ir—$H^+$-pillared | 300 | 6000 | 3000 | 3.44 | 0.04 | 4.18 |
| Ir—$H^+$-pillared | 250 | 6000 | 3000 | 2.64 | 0.02 | 3.32 |
| Ir-pillared | 300 | 6000 | 3000 | 1.25 | 0.04 | 0.90 |

EXAMPLES 47–50

The following examples were conducted in a stainless steel tube reactor heated by a Lindberg furnace. Syn gas flows were metered by a Brooks mass flow controller while liquid feeds were delivered by a Gilson or Isco pump. The catalyst was $ZrO_2$—$WO_3(18)$—Pd(0.05) and was obtained from Norton Corp. (Akron, Ohio), i.e., nominally contained 82 wt % $ZrO_2$ and 18 wt % $WO_3$. This material was supplied as an extrudate. Prior to being used, this material was calcined at 810° C. for 3 hours and was then impregnated to 0.05 wt % Pd by incipient wetness. Liquid products were collected in a condenser that was maintained at room temperature. Collected liquid products were analyzed by gas chromatography. The reaction conditions for these examples were as follows:

| | | |
|---|---|---|
| Temperature | = | 325° C. |
| Pressure | = | 1000 psi |
| Syn gas | = | 1:50 ($H_2$:CO) |
| GHSV ($hr^{-1}$) | = | 6000 |
| LHSV ($hr^{-1}$) | = | 1.5 |

The reactants and observed carbonylation products for these examples were as follows:

| Reactant | Carbonylation Products |
|---|---|
| ethanol | ethyl propionate, propionic acid |
| diethyl ether | ethyl propionate, propionic acid |
| propanol | n-butyric acid |
| n-propyl ether | n-butyric acid, propionic acid |

The foregoing description of the preferred embodiments of this invention and the examples are presented for purposes of best teaching one skilled in the art how to practice the invention. It is not, nor is it intended to be, an exhaustive description of every permutation of the invention. Obviously, many variations and modifications are possible in light of the disclosure and readily apparent to a person of ordinary skill in the art to which this invention pertains. It is intended that the full scope of the invention be defined by the appended claims.

What is claimed is:

1. A solid catalyst for the carbonylation of a feedstock comprising at least one of an alcohol, ether, ether alcohol and mixtures thereof to a product stream comprising at least one of an ester, acid, acid anhydride and mixtures thereof, by reaction thereof in the vapor state, said catalyst comprising a solid super acid impregnated with from about 0.001 to about 10 weight percent of a Group 7, 8, 9, 10 or 11 metal or mixtures thereof.

2. The catalyst of claim 1 wherein said solid super acid comprises a Group 7, 8, 9, 10 and/or 11 metal and/or mixtures thereof impregnated on a Group 4, 5 and/or 6 metal oxide and/or mixtures thereof, and wherein said solid super acid contains from about 1 to about 40 weight percent of at least one Group 6 metal oxide.

3. The catalyst of claim 1 wherein said solid super acid catalyst comprises palladium and one or more zirconium oxides in combination with one or more tungsten oxides and/or molybdenum oxides.

* * * * *